United States Patent [19]

Hartman et al.

[11] Patent Number: 4,788,203

[45] Date of Patent: Nov. 29, 1988

[54] CYCLIZED N-SUBSTITUTED-TETRAHYDROPYRIDINE COMPOUNDS, USEFUL IN THE TREATMENT OF CARDIOVASCULAR DISORDERS

[75] Inventors: George D. Hartman, Lansdale; Wasyl Halczenko, Hatfield, both of Pa.

[73] Assignee: Merck & Co., Inc., Rahway, N.J.

[21] Appl. No.: 802,127

[22] Filed: Nov. 26, 1985

[51] Int. Cl.[4] ............... A61K 31/38; A61K 31/335; A61K 31/395; C07D 471/12

[52] U.S. Cl. ............................... 514/291; 514/292; 546/84; 546/89; 546/81; 546/275; 546/283; 546/284; 540/579; 540/586

[58] Field of Search ............. 546/80, 81, 85, 256, 546/89, 84, 275, 283, 284; 514/291, 292; 540/579, 586

[56] References Cited

U.S. PATENT DOCUMENTS

| | | | |
|---|---|---|---|
| 3,905,970 | 9/1975 | Bossert et al. | 546/256 |
| 3,923,818 | 12/1975 | Bossert et al. | 546/256 |
| 4,044,141 | 8/1977 | Bossert et al. | 546/256 |
| 4,237,137 | 12/1980 | Tacke et al. | 546/256 |
| 4,285,955 | 8/1981 | Wehinger et al. | 546/256 |
| 4,505,920 | 3/1985 | Loew et al. | 546/256 |
| 4,515,799 | 5/1985 | Campbell et al. | 546/256 |
| 4,532,248 | 7/1985 | Franckowiak et al. | 546/16 |
| 4,559,350 | 12/1985 | Wehinger et al. | 546/256 |

OTHER PUBLICATIONS

Goodman et al, The Pharmacological Basis of Therapeutics, 6 Ed. p. 28.
Weller et al, J. Org. Chem. 48, pp. 3061–3067 (1983).
Goldmann, Agnew. Chem. Int. Ed. Engl., 20, pp. 779–780 (1981).

*Primary Examiner*—John M. Ford
*Assistant Examiner*—J. Richter
*Attorney, Agent, or Firm*—Alice O. Robertson; Michael C. Sudol, Jr.

[57] ABSTRACT

Novel cyclized N-substituted tetrahydropyridine compounds are disclosed. The compounds have the property of inhibiting calcium induced contraction of the smooth muscle and are adaptable to being employed in the chemotherapeutic treatment of cardiovascular diseases.

12 Claims, No Drawings

CYCLIZED N-SUBSTITUTED-TETRAHYDROPYRIDINE COMPOUNDS, USEFUL IN THE TREATMENT OF CARDIOVASCULAR DISORDERS

DESCRIPTION OF THE INVENTION

The present invention is directed to novel N-substituted tetrahydropyridine compounds cyclized through the dihydropyridine nitrogen and represented by the formula:

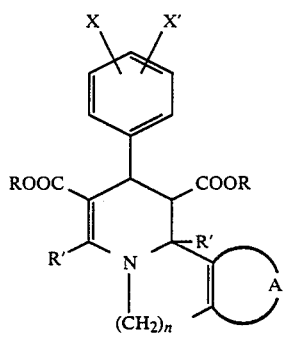
(I)

In this and succeeding formulas:

X and X' are independently hydrogen, halogen, lower alkyl, lower alkoxy, nitro or trifluoromethyl;

R is lower alkyl;

R' is lower alkyl;

A is the chain —CH=CH—Y— wherein Y is sulfur, oxygen, or substituted nitrogen; and n is 2 or 3;

and pharmaceutically acceptable salts thereof.

When Y above is nitrogen, the nitrogen is substituted with either hydrogen or lower alkyl. Thus, the chain may be —CH=CH—O—, —CH=CH—S—, —CH=CH—NH— or —CH=CH—NR"— wherein R" represents lower alkyl. The points of attachment of the chain to the heterocyclic ring may vary to provide compounds of either orientation as seen in FIGS. IA and IB.

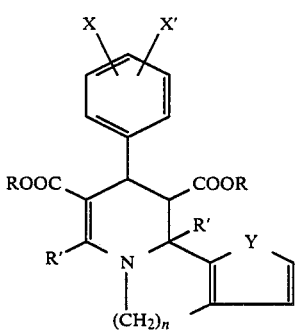
(IA)

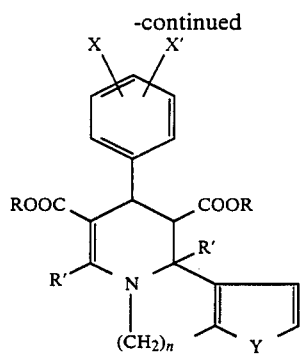
(IB)

The expressions "lower alkyl" and "lower alkoxy" refer to radicals having from 1 to 6 carbon atoms, inclusive. The expression "halogen" refers to fluorine, chlorine and bromine.

The compounds of the present invention can exist in diastereomeric forms. All such forms are included within the scope of the present invention.

The preferred compounds are those in which n is 2 and which may be represented by the formula:

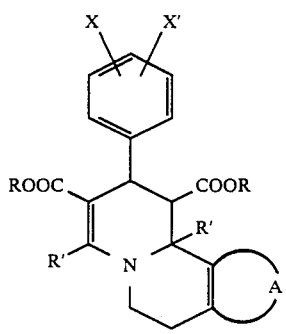
(IC)

The most preferred compounds are those compounds which may be represented by the formula:

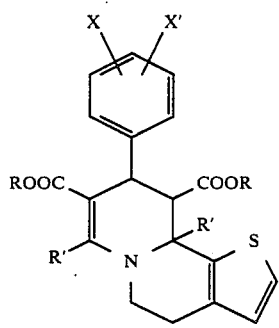
(ID)

The tetrahydro pyridine nitrogen in the compounds is basic and forms salts. The pharmaceutically acceptable salts within the scope of the present invention are acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids related to the pharmaceutically acceptable salts listed in Journal of Pharmaceutical Science, 66, 2 (1977) and incorporated herein by reference.

The compounds of the present invention are generally white crystalline solids, soluble in most organic solvents. Some of the products have been found to crystallize as hydrates.

The compounds have shown pharmacological properties which would render them useful as calcium entry blockers. The compounds of the present invention are structurally quite different from other calcium entry blockers in that the nitrogen of the tetrahydropyridine is substituted and furthermore is part of the bridge of a condensed ring system. The pharmacological properties render the compounds adaptable for application in the chemotherapeutic treatment of cardiovascular disorders caused by high cellular concentration of $Ca^{++}$. The compositions containing these compounds and methods for using the compounds as calcium entry blockers constitute an aspect of the present invention.

The compounds of Formula I may be prepared by cyclizing an appropriate N-substituted dihydropyridine compound represented by Formula II:

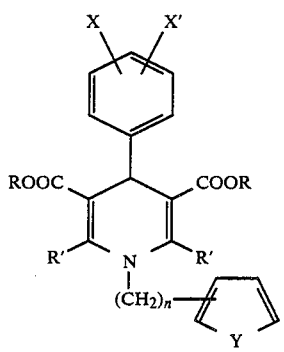

with an acid catalyst in an inert solvent under an inert atmosphere.

The starting dihydropyridine compound of Formula II may be prepared by reacting an appropriately substituted aminoalkenoate compound

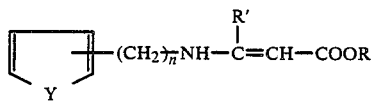

with an appropriate benzaldehyde compound

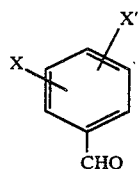

by a procedure hereinafter described and which is an application of a process fully described and claimed in copending application Ser. No. 828,474 in the name of Steven M. Pitzenberger et al. When the ultimate compound has a structure represented by (IA), the point of attachment of the tetrahydropyridyl alkyl group to the heterocyclic ring

is at the 3-position. When the ultimate compound is represented by (IB), the point of attachment is the 2-position.

The agent for the cyclization reaction to form the compound of Formula I is an acid which is employed in molar excess, from about 1.5 to 3.5 molar excess. The acid may be a conventional proton donor (Bronsted acid) or a Lewis acid. The term "Lewis acid" is meant to refer to compounds understood by the skilled artisan as reagents having either an empty or potentially empty orbital which can accept an election pair or lose a group with an electron pair in the course of reaction. Suitable acids include titanium tetrachloride, gaseous hydrogen chloride, gaseous hydrogen bromide, zinc iodide, zinc chloride, boron trifluoride, trimethylsilyl trifluoromethanesulfonate, aluminum chloride and the like. Titanium tetrachloride is especially preferred.

The reaction is carried out in an inert solvent as reaction medium. Suitable solvents are hydrocarbon solvents, including halogenated hydrocarbons such as chloroform, carbon tetrachloride, methylene dichloride, ethylene dichloride, and aromatic solvents such as benzene, toluene, xylene and the like.

The inert atmosphere is generally provided by nitrogen although other inert gases such as argon and the like, also may be employed.

The reaction is generally carried out at ambient temperature for the time sufficient for completion of the reaction. Usually from about 1 to 18 hours are employed.

In carrying out the reaction according to a preferred method, titanium tetrachloride is added with stirring at ambient temperature to a solution of the dihydropyridine compound II in an inert organic solvent in an inert atmosphere, and the stirring continued for time sufficient to substantially complete the reaction. At this time, water is added to the reaction mixture and then a sodium bicarbonate solution to neutralize the mixture. The resulting mixture is extracted with organic solvent to recover the product in the organic solution. The product is obtained from the organic solution by first washing and drying the organic solution and thereafter vaporizing the solvent and recovering the product of Formula I as residue. The product may be purified by flash chromatography (J. Org. Chem. 43, 2923 (1978)) on silica gel using hydrocarbon/ether eluant to obtain the purified product. If desired, the product may be further purified by recrystallization.

The compounds of the present invention have a property rendering them adaptable for use as calcium entry blockers in the treatment of cardiovascular disorders. The usefulness of the compounds as calcium entry blockers may be demonstrated in a nitrendipine binding assay wherein effective inhibition of nitrendipine binding is indicative of effectiveness as calcium entry blocker.

In a representative assay, 20 μg of purified sarcolemnal vesicles in 50 mM tris-HCl, 10 μM calcium chloride, and 10 μM magnesium chloride at pH 7.4 are incubated with 0.23 mM [$^3$H] nitrendipine (78 Ci/mmol) with or without test compound in a final volume of 200 μl for 3 hours at 25° C. The inhibition constant $K_i$ is determined according to the following equation $$K_i = \frac{I_{50}}{1 + \frac{[L]}{k_d}}$$

where $I_{50}$ is concentration that produces 50 percent inhibiton of binding, [L] is ligand concentration, and $k_d$ is the affinity constant of the ligand. When dimethyl 4,9,10,10a-tetrahydro-7,10a-dimethyl-9-phenyl-5H-thieno[2,3-a]quinolizine-8,10-dicarboxylate was employed, effective inhibition of nitrendipine binding was observed at concentrations as low as about $10^{-6}M$.

Effective nitrendipine binding indicates usefulness of the compounds in the study and treatment of cardiovascular diseases.

For use in the chemotherapeutic treatment of cardiovascular diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 5 milligrams to about 100 milligrams per kilogram of body weight per day. Daily doses in the range of 5 to 30 mg/kg are preferred. These doses are suitable for any of the utilities described herein.

The compound may be formulated with a pharmaceutical carrier or diluent.

To prepare the pharmaceutical compositions of this invention, a compound of Formula I is intimately admixed with a pharmaceutical carrier according to conventional pharmaceutical compounding techniques, which carrier may take a wide variety of forms depending on the form of preparation desired for administration, e.g., oral or parenteral.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques.

For parenterals, the carrier will usually comprise sterile water, although other ingredients may be included, for such purposes as, aiding solubility or preservation. Injectable suspensions also may be prepared, in which case appropriate liquid carriers, suspending agents and the like may be employed.

The concentration of the compound of Formula I in the compositions of the present invention may vary depending on whether the composition is intended for direct application or for subsequent dilution. If intended to be concentrate compositions from 2 to 95 percent active ingredient may be present. If for ultimate therapeutic application the compositions will contain, per dosage unit, e.g., tablet, capsule, powder, injection, teaspoonful and the like, from about 10 to about 500 mg of the active ingredient, preferably, from about 10 to about 250 mg.

The following examples illustrate the invention but are not to be construed as limiting.

EXAMPLE I

Dimethyl 4,9,10,10a-Tetrahydro-7,10aα-dimethyl-9β-phenyl-5H-thieno[2,3-a]quinolizine-8,10β-dicarboxylate hemihydrate

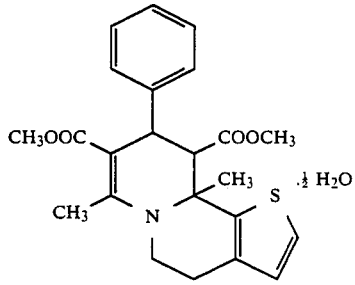

Step A: Methyl 3-[2-(3-thienyl)ethyl]aminocrotonate 3.82 grams (30 millimoles) of 3-(2-aminoethyl)thiophene was added dropwise with stirring at room temperature to 3.6 grams (31 millimoles) of methyl acetoacetate and the stirring was continued over the weekend at ambient temperature. Thereafter, the mixture was diluted with 250 milliliters of diethyl ether and the resulting ether solution washed with 50 milliliters of brine and then dried over sodium sulfate. The ether solvent was then vaporized from the dried and filtered solution to obtain 6.59 grams of a methyl 3-(3-thienylethyl)aminocrotonate intermediate as a slightly yellowish oil.

Step B: Dimethyl 2,6-dimethyl-4-phenyl-1-[2-(3-thienyl)ethyl]-1,4-dihydropyridine-3,5-dicarboxylate To 45 milliliters of benzene under a nitrogen atmosphere was added first, 0.84 milliliter (7.5 millimoles) of titanium tetrachloride and then dropwise 1.92 grams (15 millimoles) of 3-[2-(2-aminoethyl)]thiophene. The mixture became slightly warm and an orange precipitate appeared. To this mixture was added dropwise, 6.59 grams (29.2 millimoles) of freshly prepared methyl 3-(3-thienylethyl)aminocrotonate and 1.59 grams (15 millimoles) of benzaldehyde in 25 milliliters of benzene whereupon a reaction occured with the formation of a dimethyl 2,6-dimethyl-4-phenyl-1-[2-(3-thienyl)ethyl]-1,4-dihydropyridine-3,5-dicarboxylate compound as a yellow suspension. Stirring of the reaction mixture was continued at ambient temperature overnight to continue the formation of the intermediate product.

Thereafter, the reaction mixture was poured into a solvent mixture of 150 milliliters of 2N hydrochloric acid and 350 milliliters of methylene chloride, and thoroughly contacted by shaking. The aqueous and organic phases then were separated. The aqueous solution was extracted with two 100 milliliter portions of methylene chloride, the methylene chloride solutions were combined, and the combined methylene chloride solution was washed with brine and dried. The dried solution was filtered through a silica gel pad and the solvent vaporized to recover a yellow oil. 40 milliliters of hexane containing 2 milliliters of ether was added to the yellow oil and stirred at room temperature whereupon a white solid separated. A portion of the solid was recrystallized from hexane to obtain purified dimethyl 2,6-dimethyl-4-phenyl-1-[2-(3-thienyl)ethyl]-1,4-dihydropyridine-3,5-dicarboxylate intermediate product, m.p. 127.5°–128.5° C. This intermediate product had elemental analyses as follows:

Calc'd for $C_{23}H_{25}NO_4S$: C, 67.13; H, 6.12; N, 3.40. Found C, 67.01; H, 6.28; N, 3.58.

Step C: Dimethyl 4,9,10,10aα-tetrahydro-7,10a-dimethyl-9β-phenyl-5H-thieno[2,3-a]quinolizine-8,10β-dicarboxylate hemihydrate 0.49 grams (3 millimoles) of titanium tetrachloride was added with stirring to a solution of 0.41 gram (1 millimole) of dimethyl 2,6-dimethyl-4-phenyl-1-[2-(3-thienyl)ethyl]-1,4-dihydropyridine-3,5-dicarboxylate in 10 milliliters of chloroform under an atmosphere of nitrogen. Stirring was continued overnight at room temperature. Thereafter, the reaction mixture was diluted with 25 milliliters of chloroform and 25 milliliters of water, and the resulting mixture neutralized with saturated sodium bicarbonate solution. The aqueous and organic phases were separated, and the aqueous solution was extracted with three 50 milliliter portions of chloroform. The combined chloroform solution was washed with brine and then dried. The solution was placed under reduced pressure to remove the solvent whereupon a yellow solid was recovered. The latter was purified by flash chromatography on silica gel employing 1:1 hexane/ether as eluant to obtain a purified dimethyl 4,9,10,10aα-tetrahydro-7,10a-dimethyl-9β-phenyl-5H-thieno[2,3-a]quinolizine-8,10β-dicarboxylate hemihydrate product, m.p. 198°–201° C. The product had elemental analyses as follows:

Calc'd for $C_{23}H_{25}NO_4S \cdot \frac{1}{2}H_2O$: C, 65.69; H, 6.23; N, 3.33. Found: C, 65.73; H, 6.11; N, 3.05.

EXAMPLE II

Diethyl 4,9,10,10a-Tetrahydro-7,10a-dimethyl-9-(4-chlorophenyl)-5H-pyrrolo[3,2-a]quinolizine-8,10-dicarboxylate

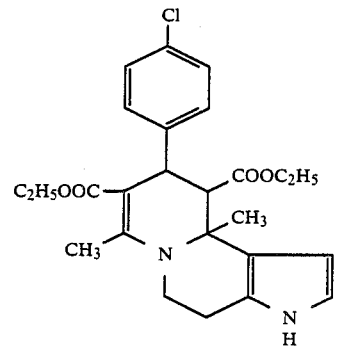

Diethyl 2,6-dimethyl-4-(4-chlorophenyl) 1-[2-(2-pyrryl)ethyl]-1,4-dihydropyridine-3,5-dicarboxylate is prepared by first reacting 11.9 grams (0.1 mole) of 2-(2-amino)ethylpyrrole and 12 grams (0.1 mole) of ethyl acetoacetate in a manner similar to that described in the preceding example to obtain about 21 grams of ethyl 3-[2-(2-pyrrylethyl)]aminocrotonate intermediate. The latter then is mixed with 7 grams (0.05 mole) of p-chlorobenzaldehyde in benzene and the resulting solution added dropwise under an atmosphere of nitrogen to a complex formed from titanium tetrachloride (4.47 grams, 0.025 mole) and 2-(2-aminoethyl)pyrrole (5.95 grams, 0.05 mole) in benzene and the resulting mixture stirred overnight. The reaction mixture is then poured into a mixture of water and methylene chloride to dissolve the dihydropyridinedicarboxylate in the organic solvent and thereafter the dihydropyridinedicarboxylate is recovered and purified employing procedures similar to that described in Example I.

0.45 gram, 1 millimole of the dihydropyridine dicarboxylate compound thus prepared is dissolved in chloroform and placed in an atmosphere of nitrogen. To it is added 0.56 gram (3 millimoles) of titanium tetrachloride in 10 milliliters of chloroform and the mixture stirred for 12 hours. At the end of this period 25 milliliters each of water and chloroform are added and the resulting mixture neutralized with saturated sodium bicarbonate solution. Then, the organic and aqueous solutions are separated, the aqueous solution is extracted with chloroform and the chloroform solution subjected to reduced pressure to vaporize the solvent and to obtain as residue a diethyl 4,9,10,10a-tetrahydro-7,10a-dimethyl(4-chlorophenyl)-5H-pyrrolo[3,2-a]quinolizine-8,10-dicarboxylate product which is purified by flash chromatography on silica gel using 1:1-hexane/ether as eluant.

EXAMPLE III

Dimethyl 4,9,10,10a-Tetrahydro-7,10a-dimethyl-9-(4-methylphenyl)-5H-furano[2,3-a]quinolizine-8,10-dicarboxylate

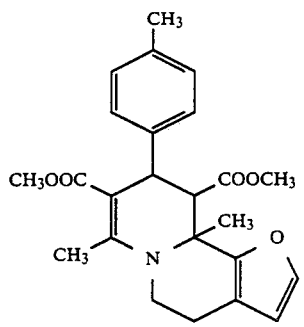

In operations carried out in a manner similar to that described in Example I and II, dimethyl 4,9,10,10a-tetrahydro-7,10a-dimethyl-9-(4-methylphenyl)-5H-furano[2,3-a]-quinolizine-8,10-dicarboxylate may be prepared by first preparing 0.1 mole of methyl 3-[2-(3-furanylethyl)]aminocrotonate by adding 0.1 mole of 3-(2-aminoethyl)furan dropwise with stirring at room temperature to (0.1 mole) of methyl acetoacetate and stirring the mixture overnight to obtain the ester in the reaction mixture and thereafter recovering the ester therefrom employing conventional procedures.

Then, dimethyl 2,6-dimethyl-4-(4-methylphenyl)-1-[2-(3-furanyl)ethyl]-1,4-dihydropyridine-3,5-dicarboxylate is prepared by adding dropwise under an atmosphere of nitrogen, a solution of 0.1 mole of methyl 3-[2-(3-furanylethyl)]aminocrotonate and 0.05 mole of benzaldehyde in 25 milliliters of benzene to a solution of 0.025 mole of titanium tetrachloride and 0.05 mole 3-(2-aminoethyl)furan in benzene and stirring for about 10 hours. Thereafter, the dimethyl 2,6-dimethyl-4-(4-methylphenyl)-1-[2-(3-furanyl)ethyl]-1,4-dihydropyridine-3,5-dicarboxy-late intermediate is recovered by working up the reaction mixture as previously described.

To a solution of 1 millimole of the dimethyl 2,6-dimethyl-4-(4-methylphenyl)-1-[2-(3-furanyl)ethyl]-1,4-dihydropyridine-3,5-dicarboxylate intermediate thus prepared is added under an atmosphere of nitrogen, 3 millimoles of titanium tetrachloride and the mixture stirred overnight at room temperature to obtain the desired dimethyl 4,9,10,10a-tetrahydro-7,10a-dimethyl-9-(4-methylphenyl)-5H-furano[2,3-a]quinolizine-8,10-dicarboxylate product in the reaction mixture. Thereafter, the mixture is diluted with 25 milliliters of chloroform and 25 milliliters of water and the product recovered therefrom in a manner similar to that previously described.

EXAMPLE IV

Dimethyl 4,9,10,10a-Tetrahydro-7,10a-di(n-propyl)-9-(4-trifluoromethylphenyl)-5H-thieno[3,2-a]quinolizine-8,10-dicarboxylate

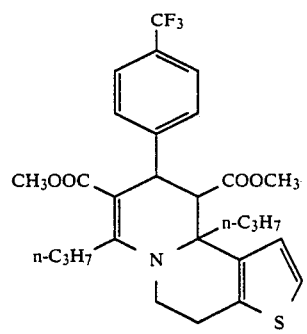

In a manner similar to that described in the preceding examples, dimethyl 2,6-di-(n-propyl)-4-(4-trifluoromethylphenyl)-1-[2-(2-thienyl)ethyl]-1,4-dihydropyridine-3,5-dicarboxylate is prepared by the reaction of (a) 2-(2-aminoethyl)thiophene and methyl butyrylacetate to obtain methyl 3-[2-(2-thienyl)ethyl]amino-2-hexenoate and (b) reacting the ester so obtained with 4-trifluoromethylbenzaldehyde in the presence of 2-(2-aminoethyl)thiophene and titanium tetrachloride.

To a solution of 1 millimole of the dihydropyridine dicarboxylate ester thus obtained in 10 milliliters of chloroform is added 3 millimoles of titanium tetrachloride under an atmosphere of nitrogen at ambient temperature and the stirring continued overnight to obtain a dimethyl 4,9,10,10a-tetrahydro-7,10a-di(n-propyl)-9-(4-trifluoromethylphenyl)-5H-thieno[3,2-a]quinolizine-8,10-dicarboxylate. The product is then recovered from the reaction mixture in the manner described in Example I.

EXAMPLE V-XV

In similar operations, the compounds in the following table may be prepared from the appropriate starting material by cyclization with titanium tetrachloride in an inert halohydrocarbon solvent under an atmosphere of nitrogen.

TABLE

| Compound | Structure Type | R | R' | X | X' | n | Y | R'' |
|---|---|---|---|---|---|---|---|---|
| V | IA | n-$C_3H_7$ | $CH_3$ | 4-(—$C_3H_7O$) | H | 3 | O | — |
| VI | IA | $C_2H_5$ | $C_2H_5$ | 4-$CH_3O$ | 3-Cl | 3 | N | H |
| VII | IA | n-$C_4H_9$ | $CH_3$ | H | H | 2 | N | $CH_3$ |
| VIII | IA | n-$C_6H_{13}$ | $CH_3$ | H | H | 2 | N | H |
| IX | IA | $CH_3$ | $CH_3$ | 2-Br | 4-Br | 2 | N | t-$C_4$—$H_9$ |
| X | IA | $CH_3$ | n-$C_6H_{13}$ | H | 3-$CF_3$ | 2 | S | — |
| XI | IB | $C_2H_5$ | $C_2H_5$ | n-$C_6H_{13}$ | H | 2 | S | — |
| XII | IB | $C_2H_5$ | $CH_3$ | 3-$NO_2$ | H | 2 | O | — |
| XIII | IB | $CH_3$ | $CH_3$ | 3-(t-$C_4H_9$) | H | 3 | S | — |
| XIV | IB | $CH_3$ | $CH_3$ | 2-F | 4-$CH_3$ | 3 | O | — |
| XV | IB | n-$C_5H_{11}$ | $CH_3$ | 4-(i-$C_3H_7$) | H | 2 | N | n-$C_6H_{13}$ |

EXAMPLE XVI 10,000 hard gelatin capsules each containing as active ingredient 25 milligrams of dimethyl 4,9,10,10a-tetrahydro-7,10a@-dimethyl-9β-phenyl-5H-thieno[2,3-a]quinolizine-8,10β-dicarboxylate hemihydrate are prepared from the following formulation:

|                    | Grams |
|--------------------|-------|
| Active ingredient  | 250   |
| Lactose            | 750   |
| Starch             | 250   |
| Talc               | 250   |
| Calcium stearate   | 10    |

A uniform mixture of the active and supplementary ingredients is prepared and filled into two-piece hard gelatin capsules. The capsules are suitable for oral administration to provide therapeutic relief for patients with cardiovascular disorders.

EXAMPLE XVII

Capsules are made by substituting for the active compound of Example XVI one of the following:
(1) diethyl 4,9,10,10a-tetrahydro-7,10a-dimethyl-9-(4-chlorophenyl)-5H-pyrrolo[3,2-a]quinolizine-8,10-dicarboxylate,
(2) dimethyl 4,9,10,10a-tetrahydro-7,10a-dimethyl-9-(p-tolyl)-5H-furano[2,3-a]quinolizine-8,10-dicarboxylate,
(3) diethyl 4,9,10,10a-tetrahydro-7,10a-dimethyl-9-(4-chlorophenyl)-5H-pyrrolo[3,2-a]quinolizine-8,10-dicarboxylate.
(4) dimethyl 4,9,10,10a-tetrahydro-7,10a-dimethyl-9-phenyl-5H-thieno[2,3-a]quinolizine-8,10-dicarboxylate hydrochloride.
(5) dimethyl 4,9,10,10a-tetrahydro-7,10a-dimethyl-9-phenyl-5H-thieno[2,3-a]quinolizine-8,10-dicarboxylate hydrogen maleate.

EXAMPLE XXVIII 5,000 compressed tablets, each containing as active ingredient 10 milligrams of dimethyl 4,9,10,10a-tetrahydro-7,10a-dimethyl-9-phenyl-5H-thieno[2,3-a]quinolizine-8,10-dicarboxylate hemihydrate are prepared from the following formulation:

|                                | Grams |
|--------------------------------|-------|
| Active ingredient              | 50    |
| Starch                         | 70    |
| Dibasic calcium phosphate hydrous | 500 |
| Calcium stearate               | 2.5   |

The ingredients are finely powdered, mixed well, and then granulated with 10 percent starch paste. The granulation is dried and compressed into tablets using starch as a disintegrant and calcium stearate as lubricant.

PREPARATION OF THE STARTING MATERIALS

The starting dihydropyridine compounds for preparing the compounds of the present invention may be prepared employing the reaction sequence depicted below or through a portion thereof depending on the availability of the precursor compounds. The preparation employs a process disclosed and claimed in the aforementioned application of Steven M. Pitzenberger, et al.

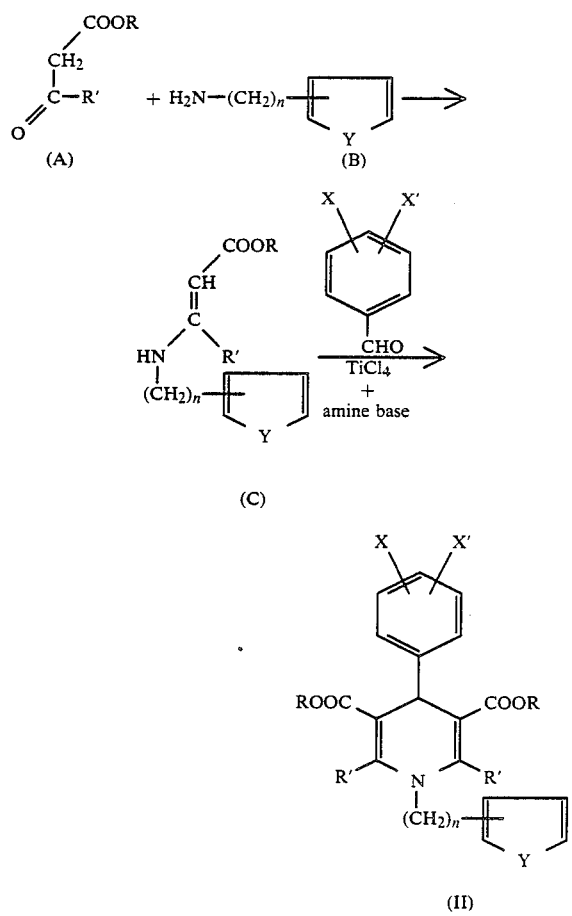

In carrying out the first step of the reaction, the appropriate aminoalkyl-heterocyclic compound (B) is added dropwise at ambient temperature to a stirred solution of alkyl acylacetate (A) and the stirring continued for time sufficient to obtain an alkyl 3-heterocycloalkylamino-2-alkenoate (C). The ester is recovered by dissolving in an ethereal solvent, conveniently, diethyl ether, and washing and drying the ether solution, then vaporizing the solvent and leaving the ester as residue.

In carrying out the second step of the reaction a benzene solution of titanium tetrachloride is prepared under an inert atmosphere and an amine base added thereto, conveniently the aminoalkylheterocyclic compound (B) employed in the preparation of the unsaturated ester compound (C). To the resulting solution is added dropwise the ester compound (C) and the appropriate benzaldehyde compound whereupon a reaction takes place with the formation of an N-substituted-1,4-dihydropyridine compound (II). The latter is recovered from the mixture employing conventional procedures.

The dihydropyridine compounds thus obtained are novel and useful not only as starting materials for the cyclized N-substituted tetrahydropyridine compounds of the present invention but are also useful as calcium entry blockers. The compounds have the property of inhibiting nitrendipine binding. Thus, for example, dimethyl 2,6-dimethyl-4-phenyl-1-[2-(3-thienyl)ethyl]-1,4-dihydropyridine-3,4-dicarboxylate exhibits effective inhibition at $10^{-6}M$. The dihydropyridine compounds also have a basic nitrogen and therefore form salts. These intermediate dihydropyridine compounds and pharmaceutically acceptable salts thereof constitute an aspect of the present invention.

What is claimed is:

1. A compound having the formula:

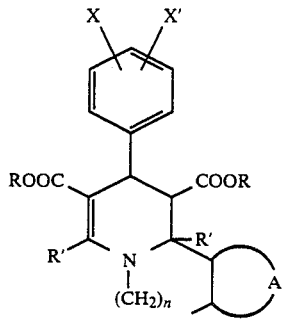

wherein
X and X' are independently hydrogen, halogen, lower alkyl, lower alkoxy, nitro or trifluoromethyl;
R is lower alkyl;
R' is lower alkyl;
A is the chain —CH=CH—Y— wherein Y is O, S, NH or NR" wherein R" is lower alkyl, and wherein the ends of said chain may be attached to the double bond in either orientation,
n is 2 or 3;
and pharmaceutically acceptable salts thereof.

2. A compound represented by the formula

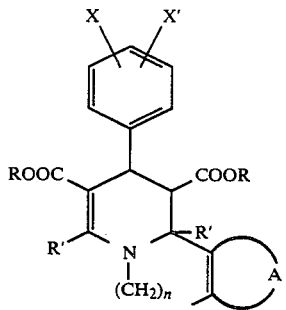

wherein
X and X' are independently hydrogen, halogen, lower alkyl, lower alkoxy, nitro or trifluoromethyl;
R is lower alkyl;
R' is lower alkyl;
A is the chain —CH=CH—O, —CH=CH—S—, —CH=CH—NH— or —CH=CH—NR" wherein R" is lower alkyl and wherein the ends of said chain may be attached to the double bond in either orientation, and
n is 2 or 3,
and pharmaceutically acceptable salts thereof.

3. A compound according to claim 1 wherein Y is S and n is 2.

4. A compound according to claim 3 wherein R and R' are methyl.

5. A compound which is dimethyl 4,9,10,10a-tetrahydro-7,10aα-dimethyl-9β-phenyl-5H-thieno[2,3-a]-quinolizine-8,10β-dicarboxylate hemihydrate.

6. A compound having the formula

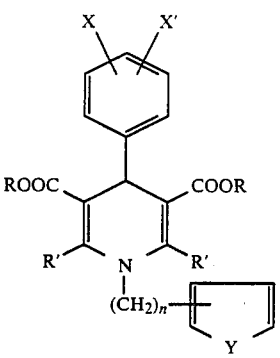

wherein
X and X' are independently hydrogen, halogen, lower alkyl, lower alkoxy, nitro or trifluoromethyl;
R is lower alkyl;
R' is lower alkyl;
Y is O, S, NH or NR" wherein R" is lower alkyl, and
n is 2 or 3,
provided that

is joined to —(CH$_2$)$_n$— through one of the carbon atoms; and pharmaceutically acceptable salts thereof.

7. A process for preparing a compound having a formula

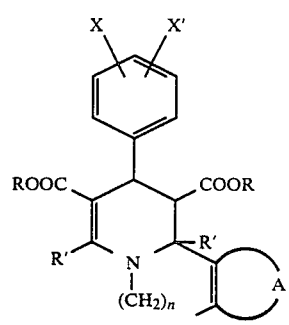

wherein
X and X' are independently hydrogen, halogen, lower alkyl, lower alkoxy, nitro or trifluoromethyl;
R is lower alkyl;
R' is lower alkyl;
A is the chain —CH=CH—Y— wherein Y is O, S, NH or NR" wherein R" is lower alkyl, and wherein the ends of said chain may be attached to the double bond in either orientation, and
n is 2 or 3;
which comprises reacting a compound having the formula

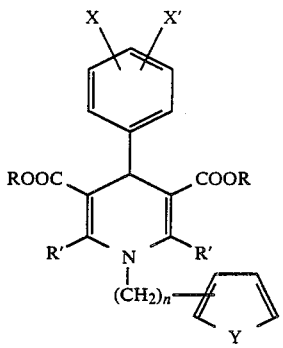

wherein

X, X', R, R, Y and n are as above defined and wherein

is attached to —(CH₂)ₙ— through one of the carbon atoms, with an acid catalyst in an inert solvent under an inert atmosphere.

8. A compound having the formula

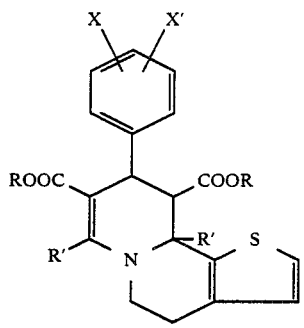

wherein
X and X' are independently hydrogen, halogen, lower alkyl, lower alkoxy, nitro or trifluoromethyl;
R is lower alkyl;
R' is lower alkyl;
and pharmaceutically acceptable salts thereof.

9. A cardiovascular pharmaceutical composition for use in the treatment of cardiovascular diseases caused by high cellular concentration of calcium consisting essentially of from 2–95 percent of a compound of claim 10 in admixture with a pharmaceutically acceptable carrier.

10. A method of treating cardiovascular disorders caused by high cellular concentration of calcium which essentially consists of administering a cellular calcium concentration inhibiting amount of a compound of claim 8.

11. A method according to claim 10 wherein the compound is administered in a dosage range of from about 5 milligrams to about 100 milligrams per kilogram of body weight per day.

12. A cellular calcium inhibiting composition for treating cardiovascular disorders which are caused by high cellular concentration of calcium which consists essentially of a compound of claim 8 in admixture with a pharmaceutically acceptable carrier wherein said compound is employed in an amount of from about 10 to 500 milligrams per dosage unit.

* * * * *